United States Patent [19]

Segawa et al.

[11] 4,236,138
[45] Nov. 25, 1980

[54] GAS COMPONENT DETECTOR

[75] Inventors: Yoshihiro Segawa, Okazaki; Minoru Ohta, Anjo; Eturo Yasuda, Okazaki, all of Japan

[73] Assignee: Nippon Soken, Inc., Nishio, Japan

[21] Appl. No.: 19,402

[22] Filed: Mar. 12, 1979

[30] Foreign Application Priority Data

Mar. 17, 1978 [JP] Japan ............................. 53-35145[U]

[51] Int. Cl.³ ............................................. H01L 7/00
[52] U.S. Cl. ..................................... 338/34; 73/27 R; 338/229
[58] Field of Search ........................... 338/34, 28, 229; 73/27 R, 23; 23/232 E; 422/98; 324/65 P, 71 SN

[56] References Cited

U.S. PATENT DOCUMENTS

| | | | |
|---|---|---|---|
| 3,959,765 | 5/1976 | Stewart | 338/34 |
| 4,001,758 | 1/1977 | Esper et al. | 338/34 |
| 4,130,797 | 12/1978 | Hattori et al. | 338/34 |
| 4,147,513 | 4/1979 | Bienkowski et al. | 73/23 |
| 4,151,503 | 4/1979 | Cermak et al. | 73/27 R |

*Primary Examiner*—C. L. Albritton
*Attorney, Agent, or Firm*—Cushman, Darby & Cushman

[57] ABSTRACT

A gas component detector has a detector element of a metal oxide held on one end of a ceramic body. The detector element is exposed to the gases to be detected and the electrical resistance value thereof is varied depending on the component of the gases. An electrical signal representing an electrical resistance value of the detector element is delivered through a pair of electrodes connected to the detector element and further through a pair of sub-lead-lines connected to the electrodes. The pairs of electrodes and sub-lead-lines are inserted in a pair of penetrating holes of the ceramic body after the electrodes and sub-lead-lines have been welded to each other. The ceramic body is inserted in a metal tube and the ceramic body and the metal tube are fixed to each other either by a tight surface contact or an adhesive. The openings of the pair of penetrating holes of the ceramic body at the opposite end with respect to the detector element are closed by a sealing material of an electrically insulating metal oxide.

5 Claims, 9 Drawing Figures

FIG. 1
FIG. 2
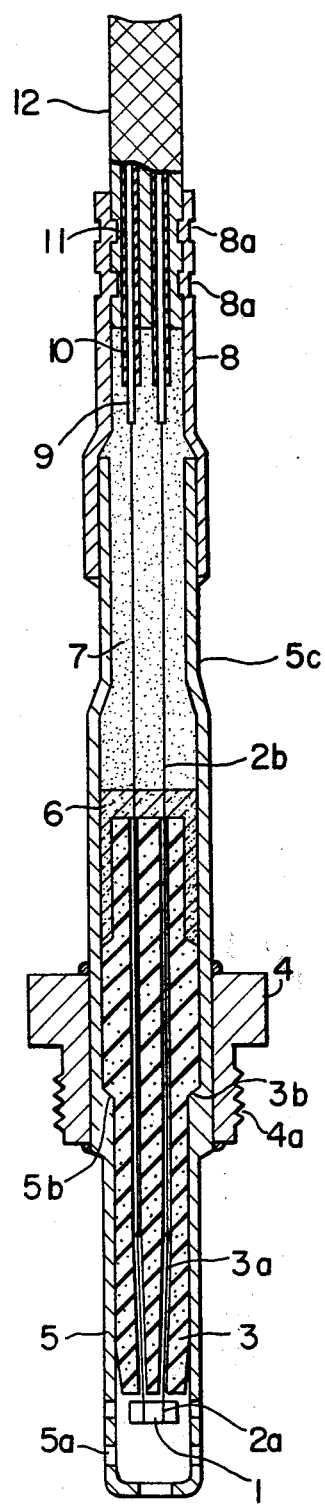
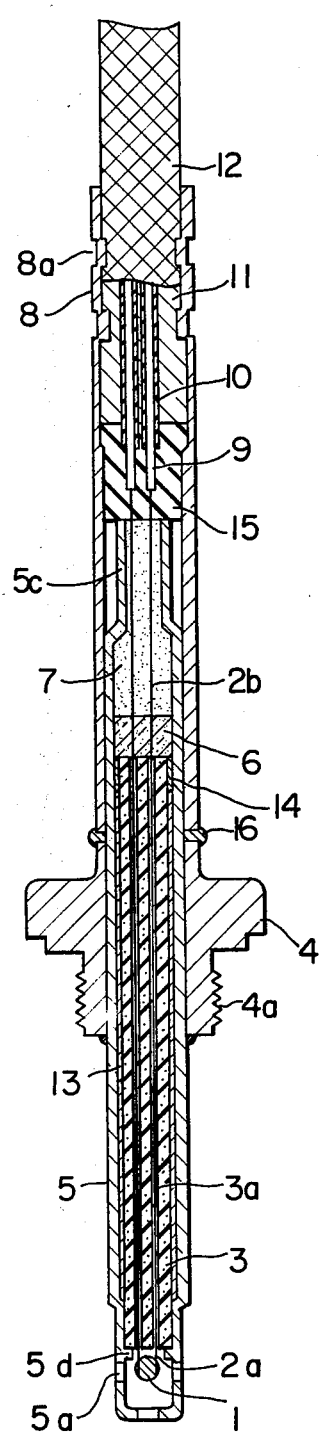

ns of the ceramic body can also be made small. Accordingly, the overall structure and size of the ceramic body, and also of the detector itself can be made small.

GAS COMPONENT DETECTOR

BACKGROUND OF THE INVENTION

1. Field of the Invention p The present invention relates to a gas component detector which may suitably be used in exhaust gas purifying systems employing a three-way catalyst for automobiles.

2. Description of the Prior Art

As gas component detectors conventionally known include those disclosed in Japanese Utility Model Laid-Open applications No. 46781/77 and No. 46792/77. These detectors are typically constituted by a detector element having a sintered body of a transition metal oxide, a pair of electrodes buried in the detector element, and a ceramic body having a pair of narrow penetrating holes to accomodate therein the pair of electrodes and having a pair of large penetrating holes to accomodate therein a pair of lead pins for delivering a signal indicative of a change in resistance value of the detector element. And a conducting glass is used between the electrodes and the lead pins to obtain electrical conduction therebetween. Further, the detectors have a housing with threads to enable them to be mounted on an exhaust pipe or the like.

By further study of the gas component detectors having the construction conventionally known as mentioned above, it has been found that several problems as follows still exist:

(1) The conductive glass is used to connect electrically the lead pins and the electrodes. However, since it is necessary to push in the lead pins and to appply pressure on the conductive glass at the melting time of the conductive glass for the purpose of filling the conductive glass uniformly in the connecting portion, lead pins having a large diameter must be used in order to widen an area under pressure. Thus, a large ceramic body is needed, and consequently, the construction of the detector itself becomes large.

(2) The ceramic body and the housing are fixed by caulking using a washer and a ring, therefore, the caulking force is apt to be insufficient, becomes loose and thus insufficiently airtight, and also sometimes the ceramic body or the detector element are broken at the time of caulking.

SUMMARY OF THE INVENTION

The present invention has an object to provide a useful gas component detector capable of overcoming the above-mentioned problems.

In this invention, electrodes and sub-lead-lines are connected by welding and they are not connected using a conductive glass as conventionally employed. Therefore, it is not necessary to use lead-pins having a large diameter to pressurize the conductive glass. As a result, the diameters of the electrodes and the sub-lead-lines can be made to be small, and hence the diameter of the pair of penetrating holes of the ceramic body can also be made small. Accordingly, the overall structure and size of the ceramic body, and also of the detector itself can be made small.

Furthermore, in this invention, the openings of the penetrating holes at the other end of the ceramic body are closed by a sealing material of a metal oxide which becomes a solid state after filling the sealing material between a metal pipe and the other end of the ceramic body. The present invention can resolve the problems and difficulties encountered in manufacturing the prior art detector in which the melting temperature and the viscosity of the conductive glass had to be considered in such a case where the conductive glass is used in both ways for sealing the penetrating holes of the ceramic body and for connecting the electrodes to the lead pins, that is, where the conductive glass serves for sealing and concurrently for electrical connection.

In addition, according to this invention, since the metal pipe and the ceramic body are fixed with each other by the surface contact between the outer surface of the ceramic body and the inner surface of the pipe having stepped portions or by the use of an adhesive, and since the sealing material is used further, the pipe and the ceramic body are sealed securely. Therefore, as compared with the sealing and fixing by caulking as conventionally used, this invention can overcome the problems such as the breakage of the ceramic body due to over caulking or the leakage through the sealed portion due to insuffficient caulking.

BRIEF DESCRIPTION OF THE DRAWINGS

FIG. 1 is a side cross-sectional view of a gas component detector according to an embodiment of this invention.

FIG. 2 is a side cross-sectional view of a gas component detector according to another embodiment of the invention.

FIGS. 3 to 9 show constructions for attaching a detector element to a ceramic body, which constructions are suitably utilized in the detectors illustrated in FIGS. 1 and 2, in which:

FIG. 3 is a side cross-sectional view of the construction;

FIG. 4 is a bottom view of the construction of FIG. 3;

FIG. 5 is a side cross-sectional view of another construction;

FIG. 6 is a bottom view of the construction of FIG. 5;

FIG. 7 is a bottom view of yet another construction;

FIG. 8 is a cross-sectional view of another construction; and

FIG. 9 is a bottom view of the construction of FIG 8.

DESCRIPTION OF THE PREFERRED EMBODIMENTS

Figure 3:
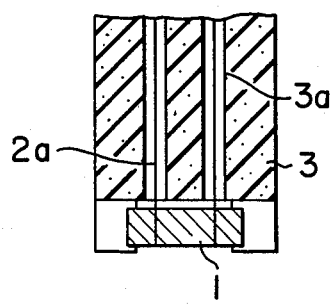

In FIG. 1, 1 is a detector element having a sintered body of a metal oxide such as titanium oxide, tin oxide or the like. 2a designates a pair of electrodes made of platinum or the like and buried in the detector element 1. 2b designates a pair of sub-lead-lines made of a heat-resistant metal such as stainless steel or the like and welded to the electrodes 2a to provide electrical conduction therebetween. 3 is a cylindrical ceramic body having a pair of narrow through holes 3a having the same diameter, and the electrodes 2a and the sub-lead-lines 2b are welded together and then inserted in the through holes 3a. The ceramic body 3 has at substantially the center thereof a portion having a larger outer diameter, and the body 3 is made of heat-resistant, electrically insulating ceramic such as alumina (aluminum oxide). 4 is a housing of a heat-resistant metal having a thread portion 4a to mount an exhaust pipe. 5 is a pipe having a plurality of holes 5a for a passage of the exhaust gas and a stepped portion 5b being in contact with a stepped portion 3b of the ceramic body 3. The pipe 5 is made of heat-resistant metal and the pipe 5 and the ceramic body 3 are fixed together at the stepped portions 3b and 5b so that they cannot move. Furthermore, this pipe 5 is welded and fixed to the housing 4 airtightly. 6 is an inorganic glass sealing material and it is filled between the ceramic body 3 and the pipe 5 to close the opening portions of the penetrating holes 3a of the ceramic body 3, and the glass sealing material 6 is in a solid state. By this glass sealing material 6, the sealing against the exhaust gas, and the fixng and insulation of the sub-lead-lines 2b are insured. 7 designates powders of alumina, magnesia or the like and serve to fix the positions of the sub-lead-lines 2b and to maintain electrical insulation therebetween. 8 is a pipe of a heat-resistant metal and is fixed by welding to the pipe 5. 9 designates a pair of lead lines connected to the sub-lead-lines 2b by welding and thus conducting therewith. The lead lines 9 are covered by a cover 10 of a heat-resistat, electrically insulating material such as a glass wool, heat-resistant rubber or the like, and, the cover 10 is also covered by another cover 11 of the same material so that the lead lines 9 are electrically insulated from each other. 12 is a cover made by knitting heat-resistant metal wires and covers the outside surface of the cover 11. This cover 12 is fixed to the pipe 8 by caulking the end of the pipe 8 as shown at 8a. Furthermore, the pipe 5 is caulked as shown at 5c at the end thereof, so that the density of the electrical insulation powders 7 filled in the pipe 5 is made high.

In the construction as described above, an electrical resistance value developed in the detector element 1 depending on a gas component in the exhaust gases can be picked up through the pair of electrodes 2a, the sub-lead-lines 2b and the lead lines 9.

FIG. 2 shows another embodiment of this invention. In FIG. 2, electrodes 2a and sub-lead-lines 2b are inserted in penetrating holes 3a after they are welded in advance as in the case shown in FIG. 1. A ring-shaped projection 5d is formed at the inside bottom of a pipe 5 of a heat-resistant metal, and a ceramic body 3 is mounted on this projection 5d. 13 is an inorganic adhesive such as Sumiceram (trade name), etc., and it becomes hard after being poured into the gap between the ceramic body 3, and the pipe 5 and owing to this adhesive 13 the ceramic body 3 and the pipe 5 are tightly fixed. 14 is a heat-resistant metal ring used for the compression of the adhesive 13. 15 is a heat-resistant rubber such as a silicone rubber disposed between the pipe 5 and the outermost cover 12 of the lead lines 9. Furthermore, the pipe 8 and the housing 4 are fixed by welding at a portion shown at 16.

Figure 5:
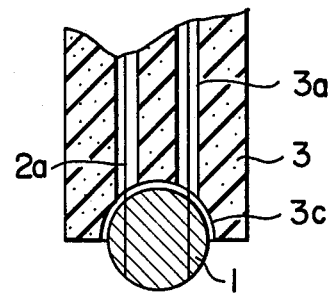
Figure 4:
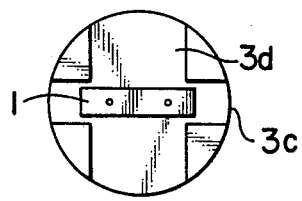
Figure 6:
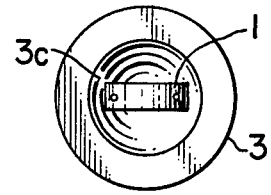
Figure 7:
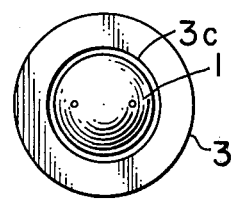
Figure 8:
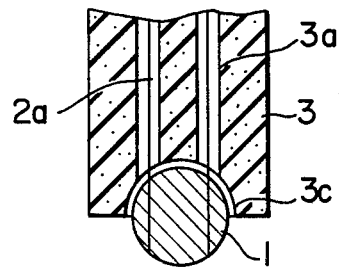
Figure 9:
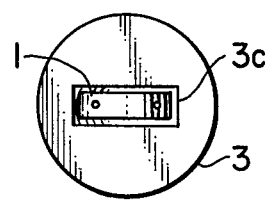

FIG. 3 to FIG. 9 show the construction for attaching the detector element 1 to the ceramic body 3 which is applicable to the embodiment described above. FIGS. 3 and 4 show an example in which a groove 3c for holding the detector element 1 therein and a groove 3d for sufficiently exposing the detector element 1 to the exhaust gases are provided on the top portion of the ceramic body 3. Since the detector element 1 is accommodated in the groove 3c, the fall of the detector element 1 due to the exhaust gas flow can be prevented. FIG. 5 shows an example in which a half spherical concave portion 3c is provided on the ceramic body 3, and FIG. 6 shows a disc-shaped detector element 1, and FIG. 7 shows a detector element 1 having a spherical shape and held in the half spherical concave 3c. FIGS. 8 and 9 show a concave 3c having a half spherical bottom surface and having a rectangular opening.

This invention is not limited to the above-described embodiments and various modifications may be made, for example, as follows:

(1) The sealing material 6 is not limited to glass, and any material may be used inasmuch as the material is an electrically insulating, heat-resistant metal oxide.

(2) The heat-resistant and electrically insulating powders 7 are not necessarily filled.

(3) This invention is not limited to the usage in automobiles and can be applied to various kinds of usage.

We claim:

1. A gas component detector comprising:
an electrically insulating and heat-resistant ceramic body having a pair of through holes penetrating axially;
a detector element of a metal oxide positioned at one end of said ceramic body, an electrical resistance value of said detector element being varied depending on a gas component in gases to be detected;
a pair of electrodes connected to said detector element and extending into said through holes at one end of said ceramic body;
a pair of sub-lead-lines connected to said pair of electrodes by welding and extending out of said through holes and therebeyond at the other end of said ceramic body;
a metal pipe fixed to said ceramic body around an outer surface thereof, said pipe extending beyond said other end of said body and terminating in a reduced end portion;
a sealing material of an electrically insulating metal oxide filled between said other end of said ceramic body and said metal pipe to close openings of said penetrating holes at said other end thereof; and
an electrically insulating powder densely packed within the extended portion of said pipe for retaining said sub-lead-line pair in fixed spaced-relation and electrically insulating said pair from each other and from said pipe.

2. A gas component detector according to claim 1, wherein said ceramic body has at said one end a groove to hold said detector element therein.

3. A gas component detector according to claim 1, wherein said ceramic body has at said one end a halfspherical concave to accommodate therein a spherical detector element.

4. A gas component detector according to claim 1, wherein said ceramic body has a sloping step portion on the outer surface between two adjacent portions of different outer diameters, and said metal pipe has on the inner surface a sloping step portion corresponding to said sloping step portion of said ceramic body between two adjacent portions of different inner diameters so that said ceramic body is mated with said metal pipe and fixed to each other by tight surface contact therebetween.

5. A gas component detector according to claim 1, wherein said ceramic body and said metal pipe are fixed to each other by an adhesive filled between the outer surface of said ceramic body and the inner surface of said metal pipe.

* * * * *